United States Patent [19]

Cohen

[11] 4,096,733

[45] Jun. 27, 1978

[54] TESTING FOOTWEAR SOLES

[75] Inventor: Arnold Cohen, Marblehead, Mass.

[73] Assignee: Jones & Vining, Incorporated, Braintree, Mass.

[21] Appl. No.: 614,250

[22] Filed: Sep. 17, 1975

[51] Int. Cl.$^2$ ............................................. G01N 3/56
[52] U.S. Cl. ....................................................... 73/7
[58] Field of Search ..................... 73/7, 9, 432 SD; 51/DIG. 13

[56] References Cited

U.S. PATENT DOCUMENTS

| 658,547 | 9/1900 | Kennedy | 73/7 |
|---|---|---|---|
| 914,431 | 3/1909 | Langenohl | 73/7 |
| 2,638,776 | 5/1953 | Aines | 73/7 |
| 3,312,100 | 4/1967 | Ainslie | 73/7 |

OTHER PUBLICATIONS

"Mechanical Walker Tests Shoe Soles"; Popular Science; Jan. 1936, p. 29.
"Physical Properties of Sole Leather; Part I"; Lloyd, D. J., et al.; in Journal of International Society of Leather Trades; Sep. 1939; pp. 461–477.

Primary Examiner—S. Clement Swisher

[57] ABSTRACT

Apparatus for testing footwear soles, comprising a frame, treadmill supports mounted on the frame for movement along an axis, a treadmill assembly mounted on the supports, the assembly including an operative treadmill surface movable in its own plane along a direction transverse to the axis, resilient means connected to the frame and the supports for biasing the treadmill surface in a rest position and for resiliently opposing movement of the surface along the axis away from the rest position to a range of operating positions, a shaft mounted on the frame, the shaft being located with its longitudinal axis parallel to the operative treadmill surface and spaced from the rest position thereof in the direction away from its range of operating positions, a drive for rotating the shaft about its axis, and a sole support mounted on the shaft at a distance from the shaft axis sufficient so that when a sole to be tested is installed on the sole support and the shaft is rotated by the drive the sole support will carry the sole along the operative treadmill surface to move the surface along its plane and, against the resilient force of the resilient means, to the range of operating positions.

12 Claims, 1 Drawing Figure

U.S. Patent   June 27, 1978   4,096,733
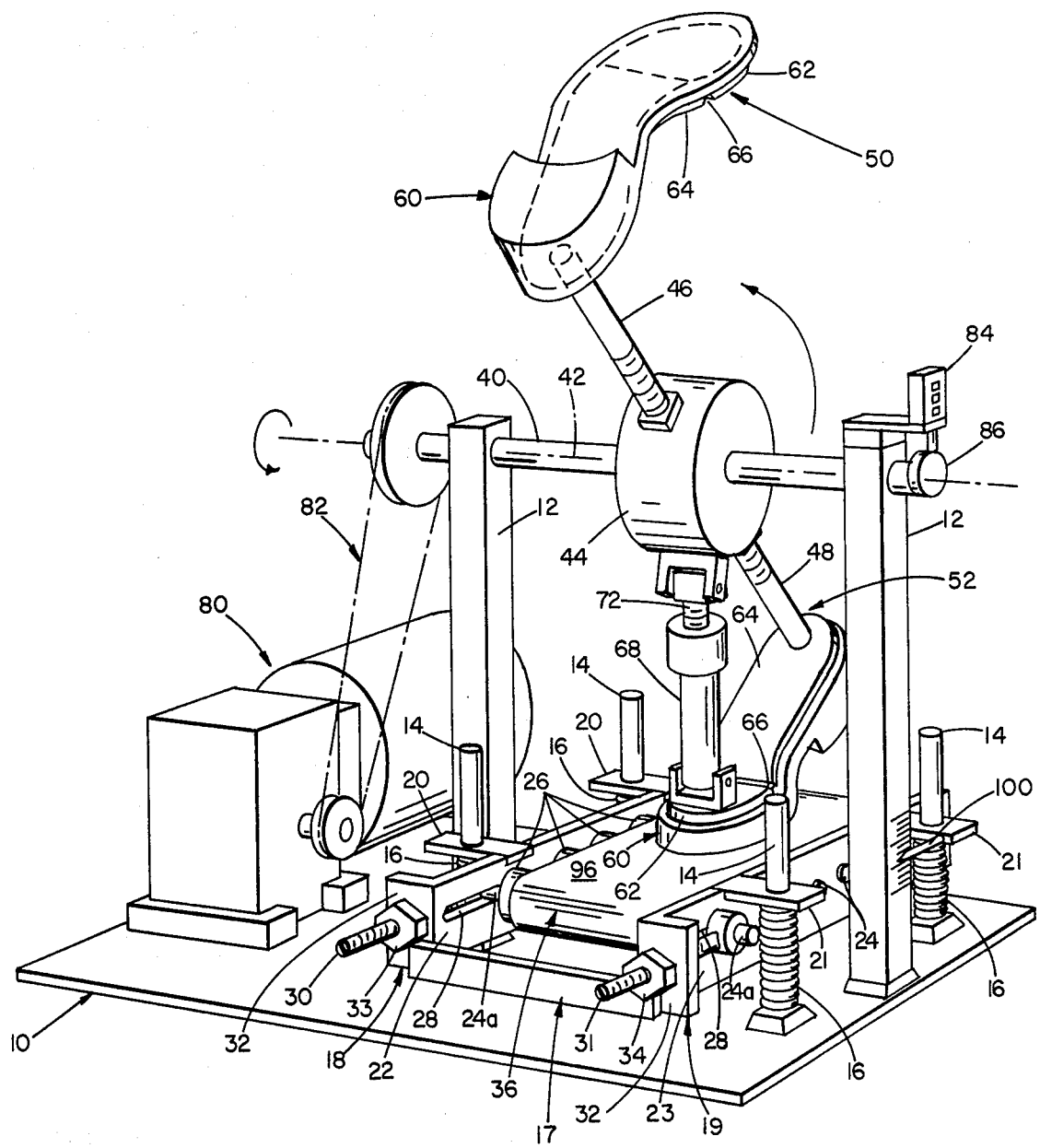

TESTING FOOTWEAR SOLES

BACKGROUND OF THE INVENTION

This invention relates to machines for testing footwear soles. Typically such machines are designed for accelerated life testing of soles under simulated conditions of actual use.

SUMMARY OF THE INVENTION

The invention provides an improved machine capable of accurately simulating a variety of conditions of actual use. The machine is rugged, easily operated, and inexpensive to manufacture, and yet provides high speed operation with sophisticated adjustable control over several parameters associated with human walking motion. The preferred embodiment is particularly designed for greatly accelerated testing of so-called unit construction soles made from a rubbery composition.

In general the invention features apparatus for testing footwear soles, comprising a frame, treadmill supports mounted on the frame for movement along an axis, a treadmill assembly mounted on the supports, the assembly including an operative treadmill surface movable in its own plane along a direction transverse to the axis, resilient means connected to the frame and the supports for biasing the treadmill surface in a rest position and for resiliently opposing movement of the surface along the axis away from the rest position to a range of operating positions, a shaft mounted on the frame, the shaft being located with its longitudinal axis parallel to the operative treadmill surface and spaced from the rest position thereof in the direction away from its range of operating positions, a drive for rotating the shaft about its axis, and a sole support mounted on the shaft at a distance from the shaft axis sufficient so that when a sole to be tested is installed on the sole support and the shaft is rotated by the drive, the sole support will carry the sole along the operative treadmill surface to move the surface along its plane and, against the resilient force of the resilient means, to the range of operating positions. In preferred embodiments the frame includes a base and a plurality of posts on the base, the posts extending through openings in the treadmill supports, and the resilient means comprises coil springs around the posts between the base and the supports; the treadmill assembly comprises a plurality of rollers having shafts carried between the supports, and an endless belt wrapped around the rollers; a plurality of sole supports are connected to the shaft through threaded rods screwed into a hub mounted on the shaft, the rods being angularly spaced for balance and adjustable radially with respect to the shaft axis; each sole support includes a sole plate with a toe portion hinged to a heel and shank portion, whereby when a sole to be tested is mounted on the sole plate and carried along the belt the sole will flex along the line of intended flexure in use on a foot; an adjustable brake is provided to vary the force necessary to move the belt over the rollers whereby the soles can be caused to at least partially slip along the belt to simulate scuffing; a counter is mounted adjacent the shaft to count its revolutions; and an indicator is provided for indicating the distance between the rest position and the operative position of the treadmill surface at any given moment in operation, whereby the indicator provides a reading of the force applied to the sole by the belt.

Other advantages and features of the invention will be apparent from the description and drawing herein of a preferred embodiment thereof.

BRIEF DESCRIPTION OF THE DRAWINGS

FIG. 1 is a semi-schematic isometric view of apparatus embodying the invention.

DESCRIPTION OF THE PREFERRED EMBODIMENT

Referring to the drawings, the main machine frame consists of a base 10, two shaft support posts 12, and four treadmill support posts 14 arranged at the corners of a rectangle between posts 12.

Each post 14 carries a coil spring 16. Treadmill support frame 17 includes support brackets 18 and 19, each with horizontal flanges 20, 21 which have holes to receive the ends of posts 14 extending above springs 16, and vertical portion 22, 23 provided with openings to receive the ends of parallel shafts 24, 24a. Each shaft 24, 24a carries a freely rotatable roller 26. The endmost shaft 24a is received in elongated slots 28 and is connected at its ends to eye bolts 30 and 31. The eye bolts extend through end flanges 32 of frame 17 and have nuts 33, 34 on their ends to form adjustable take-ups for shaft 24a. Endless neoprene belt 36 is wrapped around rollers 26 to form a treadmill. By adjusting take-up bolts 30 and 31 the horizontal position of shaft 24a, and hence the tension in belt 36, can be changed, in turn changing the force necessary to rotate the treadmill rollers (because a tighter belt increases the friction between the end rollers and their shafts). In this sense the take-ups constitute a treadmill brake.

Cross shaft 40 extends through posts 12 above the treadmill, and has its axis 42 parallel to the axes of the treadmill rollers. Hub 44 is fixed at the center of shaft 40. Radially extending adjustable threaded rods 46, 48 are screwed into the hub, 180° apart to provide a balanced assembly. Fixed to the outer end of each rod is a metal sole plate 50, 52. Each sole plate has the general shape of the sole 60 to be tested, and has a toe portion 62 connected to a shank and heel portion 64 by hinge 66 located at the line along which the sole is intended to flex in use.

A spring loaded snubber 68 is pivoted to toe portion 62 of plate 50 and is connected through adjustable threaded rod 72 to hub 44. The snubber provides additional force (beyond that provided by the inherent resilience of the sole itself) to bias toe portion 62 outwardly toward a position coplanar with portion 64. A similar snubber may be used with the other sole plate if desired.

Motor 80 is mounted on base 10 and is arranged to rotate shaft 40 through chain and sprocket drive assembly 82. Revolution counter 84 is mounted adjacent eccentric 86 on the end of shaft 40 to count its revolutions.

To operate the device described above, soles 60 to be tested are attached to plates 50 and 52, e.g., with contact cement, or even with straps (not shown) located in areas not intended to contact the treadmill. Rods 46, 48 and 72 are adjusted so that when shaft 40 is rotated by motor 80, plates 50 and 52 will carry soles 60 along and press them against the upper operative surface 96 of the treadmill belt, compressing springs 16 so that a selected amount of back force against the sole bottoms is exerted through belt 36. A pointer 100 is mounted on flange 21 and cooperates with graduations on post 12 to indicate the amount by which springs 16 are compressed, and hence the reaction force applied to the soles. That force can be increased by adjusting the sole plates to positions radially farther out from hub 44.

As the soles pass over the treadmill, they will flex along the lines of hinges 66. That flexure (the resistance to which can be adjusted in the case of plate 50 by adjusting snubber rod 72 in hub 44), along with the resilient quality of the treadmill provided by springs 16, closely simulates the flexure and sole compression of actual walking conditions. Furthermore, a controlled degree of scuffing can be introduced by tightening take-up bolts 30 and 31 so that belt 36 resists movement sufficiently to cause the soles to at least partially slip along surface 96. The ability to apply substantial force against the sole bottoms greatly accelerates the testing process.

A variety of surface conditions can be simulated by applying substances such as oil or abrasives to belt 36.

Other embodiments are within the following claims.

What is claimed is:

1. Apparatus for testing footwear soles, comprising a frame,
   treadmill supports mounted on said frame for movement along an axis,
   a treadmill assembly mounted on said supports, said assembly including an operative treadmill surface movable in its own plane along a direction transverse to said axis,
   resilient means connected to said frame and said supports for biasing said treadmill surface in a rest position and for resiliently opposing movement of said surface along said axis away from said rest position to a range of operating positions,
   a shaft mounted on said frame, said shaft being located with its longitudinal axis parallel to said operative treadmill surface and spaced from said rest position of said surface in the direction away from its said range of operating positions,
   a drive for rotating said shaft above its said axis, and
   a sole support mounted on said shaft at a distance from said shaft axis sufficient so that when a sole to be tested is installed on said sole support and said shaft is rotated by said drive, said sole support will carry said sole along said operative treadmill surface to move said surface along its said plane and, against the resilient force of said resilient means, to said range of operating positions,
   said frame including a base and a plurality of posts on said base, said posts extending through openings in said treadmill supports, said resilient means comprising coil springs around said posts between said base and said supports.

2. The apparatus of claim 1 wherein said sole support includes a sole plate with a toe portion hinged to a heel and shank portion, whereby when a sole to be tested is mounted on said sole plate and carried along said operative treadmill surface said sole will flex along the line of intended flexure in use on a foot.

3. The apparatus of claim 1 wherein said sole support is connected to said shaft through a member adjustable radially with respect to said shaft axis.

4. The apparatus of claim 3 wherein said shaft has a hub mounted thereon, and said member is a threaded rod screwed in said hub.

5. The apparatus of claim 4 wherein a plurality of said sole supports are provided, each having a said threaded rod screwed in said hub, said rods being angularly spaced about said shaft axis to provide a balanced assembly.

6. The apparatus of claim 1 further comprising a brake adjustable to vary the force necessary to move said operative treadmill surface along its said plane, whereby said soles can be caused to at least partially slip along said operative surface when said shaft is rotating, to simulate scuffing.

7. The apparatus of claim 1 wherein said treadmill assembly comprises a plurality of rollers having shafts carried between said supports, and an endless belt wrapped around said rollers.

8. Apparatus for testing footwear soles, comprising a frame,
   treadmill supports mounted on said frame for movement along an axis,
   a treadmill assembly mounted on said supports, said assembly including an operative treadmill surface movable in its own plane along a direction transverse to said axis,
   resilient means connected to said frame and said supports for biasing said treadmill surface in a rest position and for resiliently opposing movement of said surface along said axis away from said rest position to a range of operating positions,
   a shaft mounted on said frame, said shaft being located with its longitudinal axis parallel to said operative treadmill surface and spaced from said rest position of said surface in the direction away from its said range of operating positions,
   a drive for rotating said shaft about its said axis, and
   a sole support mounted on said shaft at a distance from said shaft axis sufficient so that when a sole to be tested is installed on said sole support and said shaft is rotated by said drive, said sole support will carry said sole along said operative treadmill surface to move said surface along its said plane and, against the resilient force of said resilient means, to said range of operating positions,
   said treadmill assembly comprising a plurality of rollers having shafts carried between said supports, and an endless belt wrapped around said rollers,
   means being provided for adjusting the position of one of said shafts to vary the force necessary to move said operative treadmill surface along its said plane, whereby said soles can be caused to at least partially slip along said operative surface when said shaft is rotating, to simulate scuffing.

9. The apparatus of claim 1 further comprising a counter mounted adjacent said shaft to count its revolutions.

10. The apparatus of claim 1 further comprising an indicator for indicating the distance between said rest position and the operative position of said treadmill at any given moment in operation, whereby said indicator provides a reading of the force applied to said sole by said operative surface.

11. Apparatus for testing footwear soles, comprising
   a frame having a base and a plurality of posts on said base,
   treadmill supports mounted on said frame for movement along an axis, said supports having openings through which said posts extend,
   coil springs mounted around said posts between said base and said supports to bias said supports in the direction away from said base,
   a treadmill assembly comprising a plurality of rollers each having shafts carried between said supports, and an endless belt wrapped around said rollers to define an operative treadmill surface movable in its own plane along a direction transverse to said axis, said coil springs thereby acting to bias said treadmill surface in a raised position and to resiliently oppose movement of said surface along said axis away from said raised position to a range of operating positions, a shaft mounted on said frame, said shaft being located with its longitudinal axis parallel to said operative treadmill surface and spaced away from said raised position in the direction away from said range of operating positions, a drive for rotating said shaft about its said axis, a hub mounted on said shaft, a plurality of threaded rods screwed in said hub, said rods being angularly spaced about said shaft axis to provide a balanced assembly and being adjustable radially with respect to said shaft axis, a plurality of sole plates respectively connected to the free ends of said threaded rods, each said sole plate having a toe portion hinged to a heel and shank portion, said rods and said sole plates being located such that when soles to be tested are installed on said sole plates and said shaft is rotated by said drive, said sole plates will carry said soles along said operative treadmill surface to move said surface along its said plane and, against the resilient force of said resilient means, to said range of operating positions, the hinged arrangement of said toe portion causing said sole to flex along the line of intended flexure in use on a foot, and means for adjusting the position of one of said shafts of said treadmill assembly to vary the force necessary to move said operative treadmill surface along its said plane, whereby said soles can be caused to at least partially slip along said operative surface when said shaft is rotated, to simulate scuffing.

12. A testing device comprising an articulated sole plate to which a bottom member to be tested is adapted to be attached, said sole plate being articulated at substantially the ball line, a tread surface with which the bottom member is repeatedly brought into engagement to simulate the wear produced by walking and means for repeatedly bringing the shoe body member into engagement with said tread surface comprising a rigid member fixed at one end to the heel end of the sole plate, a yieldable member connected at one end to the toe end of the sole plate which holds the articulated toe portion distended in the plane of the heel portion, a rotor rotatable about a fixed axis parallel to the tread surface to which the opposite ends of the rigid and yieldable members are connected such that they radiate from the axis of the rotor and means for rotating the rotor in a direction to first bring the heel end of the shoe bottom member into engagement with the tread surface and then the toe end.

* * * * *